(12) United States Patent
Hartstock-Martin

(10) Patent No.: US 9,498,045 B2
(45) Date of Patent: Nov. 22, 2016

(54) APPLICATOR WITH BRISTLE-ENDED CARTRIDGES

(71) Applicant: GEKA GmbH, Bechhofen (DE)

(72) Inventor: Karl Hartstock-Martin, Ansbach (DE)

(73) Assignee: GEKA GmbH, Bechhofen (DE)

( * ) Notice: Subject to any disclaimer, the term of this patent is extended or adjusted under 35 U.S.C. 154(b) by 55 days.

(21) Appl. No.: 14/557,983

(22) Filed: Dec. 2, 2014

(65) Prior Publication Data

US 2015/0182002 A1    Jul. 2, 2015

(30) Foreign Application Priority Data

Dec. 27, 2013  (DE) .................. 20 2013 011 647 U

(51) Int. Cl.
| | |
|---|---|
| *B43K 5/02* | (2006.01) |
| *A45D 34/04* | (2006.01) |
| *A46B 11/00* | (2006.01) |
| *A45D 19/02* | (2006.01) |
| *A45D 24/28* | (2006.01) |
| *A61M 35/00* | (2006.01) |
| *A45D 34/00* | (2006.01) |

(52) U.S. Cl.
CPC ............ *A45D 34/042* (2013.01); *A45D 19/02* (2013.01); *A45D 24/28* (2013.01); *A46B 11/0003* (2013.01); *A46B 11/0055* (2013.01); *A46B 11/0062* (2013.01); *A61M 35/003* (2013.01); *A45D 2034/005* (2013.01); *A45D 2200/055* (2013.01)

(58) Field of Classification Search
CPC .......... A46B 11/0003; A46B 11/0055; A46B 11/0062; A45D 2200/055; A45D 2034/005; A45D 34/042; A45D 24/28
USPC ................................ 401/188 R, 277; 433/80
See application file for complete search history.

(56) References Cited

U.S. PATENT DOCUMENTS

| | | | |
|---|---|---|---|
| 1,742,157 A | 2/1929 | Christian | |
| 4,139,312 A | 2/1979 | Marano et al. | |
| 6,743,015 B2 * | 6/2004 | Magnani ............. | A61C 19/063 433/80 |
| 8,262,302 B1 * | 9/2012 | Bouix ................. | A45D 40/267 401/1 |
| 8,387,628 B2 * | 3/2013 | Bowie ................ | A46B 11/0027 132/311 |
| 9,022,680 B1 * | 5/2015 | Lubyanitskiy ..... | A46B 11/0086 401/142 |
| 2004/0035435 A1 | 2/2004 | Glucksman et al. | |

FOREIGN PATENT DOCUMENTS

| | | |
|---|---|---|
| CN | 101637332 A | 2/2010 |
| DE | 2830480 | 1/1980 |
| FR | 1555567 A | 1/1969 |
| FR | 2588734 A3 | 4/1987 |
| FR | 2772569 A1 | 6/1999 |
| GB | 691593 A | 5/1953 |
| WO | 9851183 | 11/1998 |

OTHER PUBLICATIONS

German Search Report in related German Utility Model application 20 2013 011 647.1 filed Dec. 27, 2013.

\* cited by examiner

*Primary Examiner* — Jennifer C Chiang

(74) *Attorney, Agent, or Firm* — Polson Intellectual Property Law, PC; Margaret Polson

(57) ABSTRACT

Cosmetic or pharmaceutical applicator with a supply of the cosmetic or pharmaceutical fluid provided in the brush outside of the bristle facing, a pump mechanism for dispensing the fluid through or in the bristle facing of the brush, whereupon the bristle facing of the brush is a fixed component of a cartridge which provides a supply of the fluid and which can be inserted into and removed again from the applicator chamber intended for this purpose, preferably without the use of tools.

14 Claims, 12 Drawing Sheets

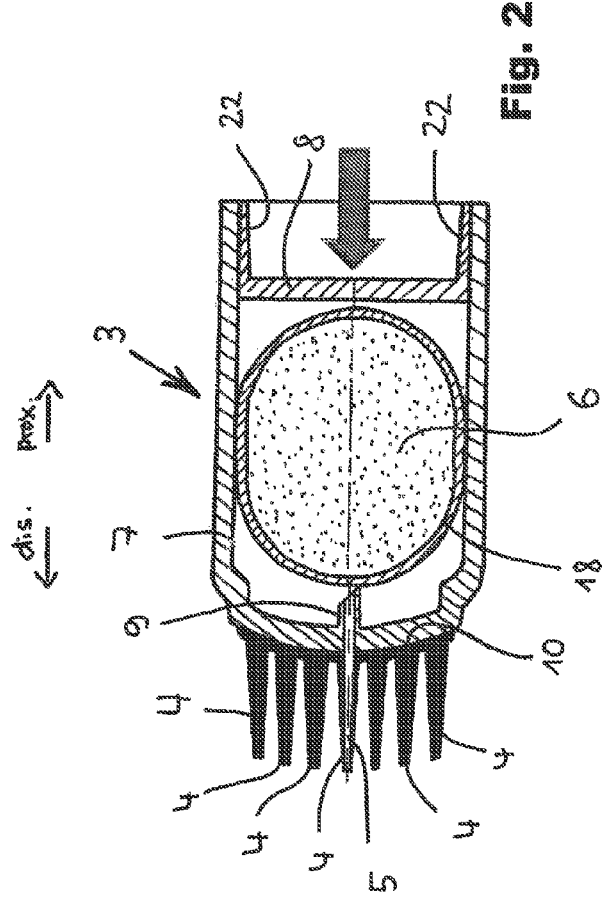
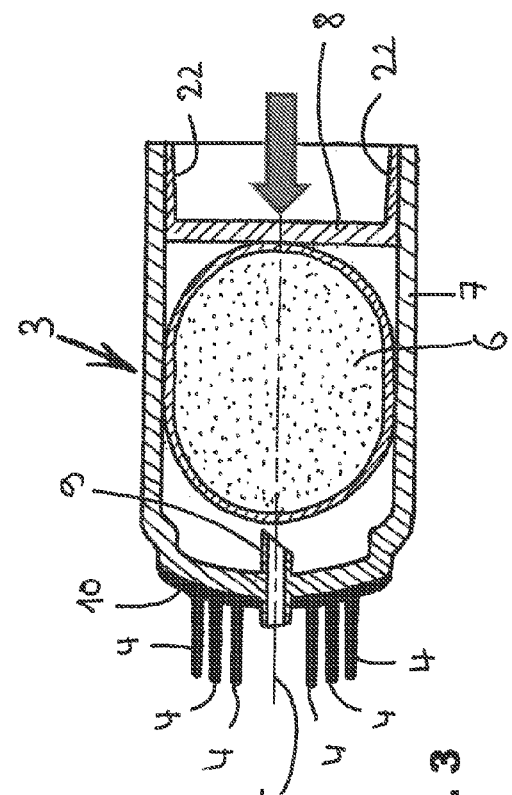
Fig. 2
Fig. 3

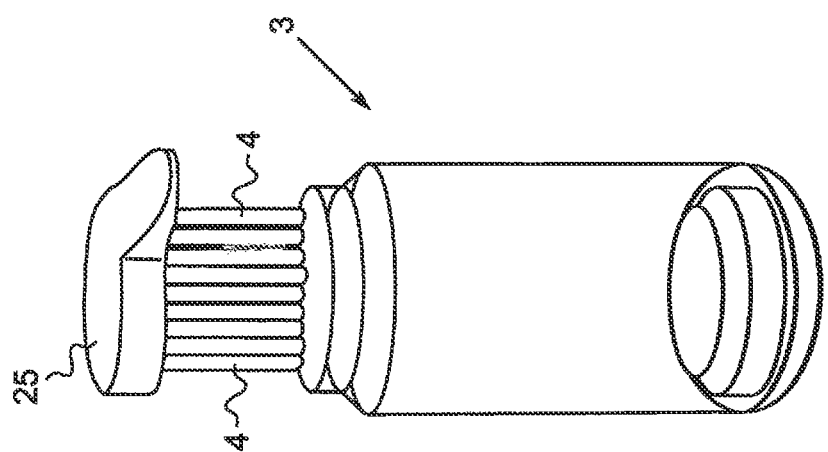
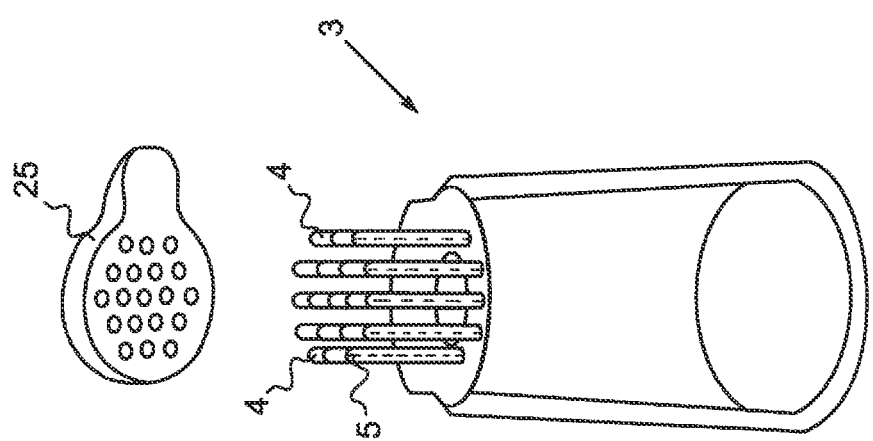

APPLICATOR WITH BRISTLE-ENDED CARTRIDGES

CROSS REFERENCE APPLICATIONS

This application claims the benefit of German Application No. 20 2013 011 647.1 filed Dec. 27, 2013, which is incorporated herein by reference for all purposes.

BACKGROUND

Low-viscosity pharmaceutical or cosmetic compositions are often applied with the aid of a brush. If nothing else, this can cause difficulties in areas where pharmaceutical or cosmetic compositions are to be applied to hair-covered skin. Hair restorers are a typical example of this.

The application of such substances onto hair-covered skin normally leads to considerably more of the substance being used as is good for the skin, due to the fact that a good part of the substance to be applied gets caught up in the hair. The cosmetic substance is therefore lost or may even cause the hair to stick together and thus have a disruptive impact.

As an alternative to a brush, a cotton bud is often used to apply pharmaceutical or cosmetic substances to hair-covered skin. It is normally dipped in the substance to be applied and an attempt is then made to act on the hair-covered skin while avoiding the hairs. Such a method at least reduces the amount of pharmaceutical or cosmetic that gets caught in the hair. Nevertheless, the amount consumed is still relatively high as the cotton bud has a relatively high absorbency and therefore draws in a good amount of the pharmaceutical or cosmetic substance, but does not release it again.

Due to this, the idea has already been considered to apply pharmaceutical or cosmetic substances to hair-covered skin with the aid of a relatively hard brush. This allows for a reduction in the amount of cosmetic or pharmaceutical that adheres to the hair and is of no benefit to the skin. As long only the tip of the brush is covered with the cosmetic or pharmaceutical to be applied, the amount of substance used can also be reduced in comparison to application with the cotton bud. However, a problem arises here due to the fact that the brush used for application is normally not discarded, but instead must be cleaned and then painstakingly dried, for example. And such a cleaning method is also not entirely unproblematic from a hygiene viewpoint as a brush can almost never be cleaned one-hundred percent.

Furthermore, in particular when it comes to expensive pharmaceutical or cosmetic substances, such as hair restorers, the aim is to further reduce consumption.

The foregoing example of the related art and limitations related therewith are intended to be illustrative and not exclusive. Other limitations of the related art will become apparent to those of skill in the art upon a reading of the specification and a study of the drawings.

SUMMARY

This task is solved using a cosmetic or pharmaceutical applicator with as described herein. In the invented brush, the supply of the cosmetic or pharmaceutical fluid to be applied is held ready outside of the bristle facing. The disclosed applicator has a pump mechanism for dispensing the fluid into the bristle facing, preferably through one or more bristles.

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Thereby, the bristle facing of the brush is a fixed component of a cartridge which keeps the supply of fluid ready for use and which, together with the bristle facing, forms a component part which is independent and can be handled separately from the other parts of the applicator. This cartridge can be preferably inserted into and removed from an applicator compartment provided for this purpose without the use of tools. If required, very sensitive dosing can be achieved with the aid of the pump mechanism. The aforementioned dosing can either be achieved by the fact that the cartridge only contains the amount of fluid required for one application, or alternatively, the pump mechanism can be driven in such a way that, once triggered, it only dispenses a predetermined amount of fluid from the cartridge which only holds a fluid amount to suffice for several applications.

The fluid is dispensed into the bristle facing. This prevents fluid from "missing the mark" even before the brush comes into contact with the skin area to which the fluid is to be applied. For the invented brush, at least in its motor-driven variant, makes it possible to firstly bring the brush into contact with the skin area and then to start up the pump mechanism. This noticeably improves the application result when applying the substance in both hair-covered and hair-free areas.

The invention displays its advantages even better if the fluid is not dispensed in the area of the bristle base into the bristle facing, but rather if the fluid is dispensed through at least one hollow bristle into the area of the bristle tips. For then the fluid is brought as close as at all possible to the skin area to be treated so that only minimum losses can be feared. In particular, in such a design, no loss arises through to a considerable amount of fluid getting caught in the bristle facing of the brush. The fluid is dispensed through the hollow bristle (N) directly at one or more bristle tips, meaning that it adheres immediately and follows the shortest possible route to the scalp. Thus, the bristles are no longer a means of supplying the fluid to the scalp area, i.e., as a means of initially storing the fluid between the bristles and then, when in contact with the hair-covered skin, releasing it more or less completely. Instead the bristles are essentially only used for massaging in and distributing the fluid which has already adhered to the scalp.

With the aid of the invented cartridge, the problem of how to durably seal the area in which the fluid is stored is solved well. For in all kinds of applicators which accommodate a supply of the fluid to be applied, there is always the problem of leaks occurring once a device has been operated for a period of time due to the fact that the seals, which cannot be extremely expensive so as not to force the cost of the applicator into an unacceptable price range, become worn. This is counteracted in the invented cartridge solution. Even if the seals become worn, this does not mean that the entire applicator needs to be discarded—it is enough to renew the cartridge.

For both this reason and for hygiene reasons, it is particularly recommended to supply the cartridge in a disposable design. For then, the strengths of the invention can be implemented to their full potential. Due to the fact that the bristle facing is a fixed component of the cartridge, when the cartridge is replaced the bristle facing is automatically replaced, too. This way, the applicator is not only always "well filled", but also always has a bristle facing which is hygienic and in good shape. The bristles can be designed to be softer than in an applicator which has to withstand dozens of applications without the bristles being allowed to become deformed. The disadvantages as such linked to the use of quite a soft bristle facing can be mastered well here as the finite contents of the cartridge mean that it is possible to determine very precisely how many applications the bristles need to withstand without succumbing to excessive deformations.

The use of disposable cartridges is also particularly advantageous in areas where high hygiene requirements are called for, or where even sterile use is necessary. In this case, disposable cartridges are used which only accommodate a storage volume amounting to precisely, or at least essentially, the fluid quantity required for one single application. After the single application, the cartridge including the bristle facing are discarded immediately and replaced for the next application with a new cartridge which also has a new bristle facing.

Sterility can be ensured using this method. It is in fact even easier to guarantee almost one-hundred percent sterility than with a separate brush which is immersed into a reservoir. For here in the invented system, the bristle facing remains sterile until it comes into contact with the scalp and only then is the fluid dispensed. The necessity of immersion into a fluid and the connected risks of potential multiple immersion and the related transfer of germs are omitted.

Special preference is given to each of the invented cartridges, when unused, accommodating a capsule which is made up a hermetically completely sealed shell filled with the fluid to be applied. This is another way of ensuring increased sterility and/or omitting the negative effects of the surrounding area on the fluid (in particular air admission) as far as possible.

The cartridge should preferably have a mandrel protruding into its interior area holding the capsule. This mandrel punctures the capsule once the pump mechanism for dispensing the cosmetic is started up and the capsule is pressed against the mandrel. It is particularly preferable that the mandrel has a non-rotund cross-section, but rather a cross-shaped one. Such a cross-section means that the capsule is not sealed by the external circumference of the mandrel with the result that fluid can only escape through the hollow internal section of the mandrel, but rather that the fluid can escape from the capsule into the entire interior of the cartridge. Such a design always makes sense in cases where the fluid from the capsule is not discharged outwards through one single hollow bristle, but through multiple bristles which are hollow on the inside and which each form a connection between the interior of cartridge 3 and the surrounding area.

Preferably, the cartridge essentially comprises a harder first plastic material which creates at least the perimeter walls and an end wall of the cartridge, and a softer, preferably soft plastic or rubber-like second plastic which forms the bristles inseparably connected to the cartridge. The cartridge and the bristles injection-molded onto it are thus manufactured in two consecutive injection-molding steps. Such a production method and the resulting product properties allow both the cartridge and the bristles to optimally adapt to their respective function. The cartridge must be made of harder plastic to make it resistant to deformation and also withstand a certain amount of internal pressure. The bristles, on the other hand, must often be as soft and elastic as possible so as not to unnecessarily aggravate the hair-covered skin areas or to create an unpleasant feeling.

Preferably, the bristle facing has at least one, and ideally only one, bristle which is hollow inside and which thus forms the bristle channel connecting the interior area of the cartridge holding the fluid to be applied to the surrounding area of the cosmetic brush. The fluid can be dispensed with particular efficiency this way. The fluid emerges at the outermost tip of the at least one/only one bristle. The bristle facing cannot therefore be soaked in fluid and cannot retain a large portion of the fluid instead of releasing it onto the skin. Instead, the bristle facing is predominantly aimed at distributing the fluid onto the skin, whereupon mostly only the tips of the bristles forming the bristle facing (approximately the outermost third of the bristles) actually come into more than just insignificant contact with the fluid to be applied. This type of design is of particular benefit in such cases where the cartridge body and the bristle facing positioned at its front end are injection molded in one piece using the same, uniform plastic, preferably in one shot. For this is the easiest way to injection-mold a bristle with a hollow interior using a molding pin (diameter≤1.5 mm, better≤1 mm).

Preferably, while taking into account the viscosity and capillary action of the fluid, the bristle channel is be shaped narrow enough, so that the fluid contained in the cartridge is prevented by the capillary action of the fluid from unintentionally escaping via the bristle channel and into the open, as long as the contents of the cartridge are not put under excessive pressure. This can prevent unintentional leakage from an applicator which, for example, is not set down on its head during a break in treatment, but rather has been inadvertently put down on its side.

For other applications, it is particularly favorable if the inside of the end wall of the cartridge is at least partially covered with a layer of the plastic which forms the bristles, whereupon the plastic which forms the cartridge is locally perforated to form a one-material and one-piece connection between this layer and bristles which freely protrude outwards.

This way, the bristle facing can not only be manufactured very effectively but can in particular also be securely anchored onto the cartridge, particularly if it is made of a different material to the cartridge body. Preferably, the cartridge has a base and a cartridge plunger which can be moved in similar way to a piston, on the edge side facing away from the bristle facing. This cartridge plunger is preferably manufactured from a third plastic, the flexibility of which is ideally between the flexibility of the plastic used for the bristles and the flexibility of the plastic forming the perimeter wall of the cartridge. This way, the cartridge plunger can be designed to have particularly good spring characteristics so that, after it is fitted, it can be pretensioned in the area forming the cartridge perimeter wall and thus rest closely against it.

A preferred design envisages that the brush compartment incorporating the cartridges is accessible through the fact that a part of the top of the applicator body can be flipped open from the applicator main body using a hinge axis which is essentially perpendicular to the longitudinal axis of the applicator. When opened in such a way, this very quickly creates an easily accessible opening for the removal and insertion of cartridges. Laborious screwing-on is omitted.

For many applications, it is particularly useful if a vibrator which causes the bristle facing or the entire applicator to vibrate is installed in the applicator. Ideally, this is a mass oscillator which induces vibrations at a slant or in a fundamentally perpendicular direction in relation to the applicator's longitudinal axis, preferably at a frequency of more than 6 Hz and an amplitude of less than 1 mm.

Independent protection is also required for a system for the application of a pharmaceutical or cosmetic comprising an applicator of the type characterized above and a number of ideally tool-free, non-refillable cartridges with a bristle facing formed onto them, each of which holds a supply of the pharmaceutical or cosmetic to be applied and is customized to suit the cartridge holding compartment of the applicator.

This system is ideally expanded to include a blister pack which holds several cartridges to form a cartridge supply. At the same time, the blister pack is designed so that each of the cartridges can be removed individually from the blister pack, which is preferably transparent on one side or ideally sealed with a metal foil on the reverse, without already subjecting the other cartridges to largely unhindered air admission, or the largely unhindered impact of environmental influences.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE DRAWINGS

FIG. 1a shows a detailed excerpt from FIG. 1.

FIG. 2 shows an individual illustration of a cartridge, as it is used as an alternative, along the longitudinal axis.

FIG. 3 shows an individual illustration of a cartridge, as it is used as another alternative, along the longitudinal axis.

FIG. 9 shows an individual view of the cartridge, as it is described within the framework of the first design example.

FIG. 10 shows the cartridge according to FIG. 9, with the cap on.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION OF THE DRAWINGS

Figure 1:
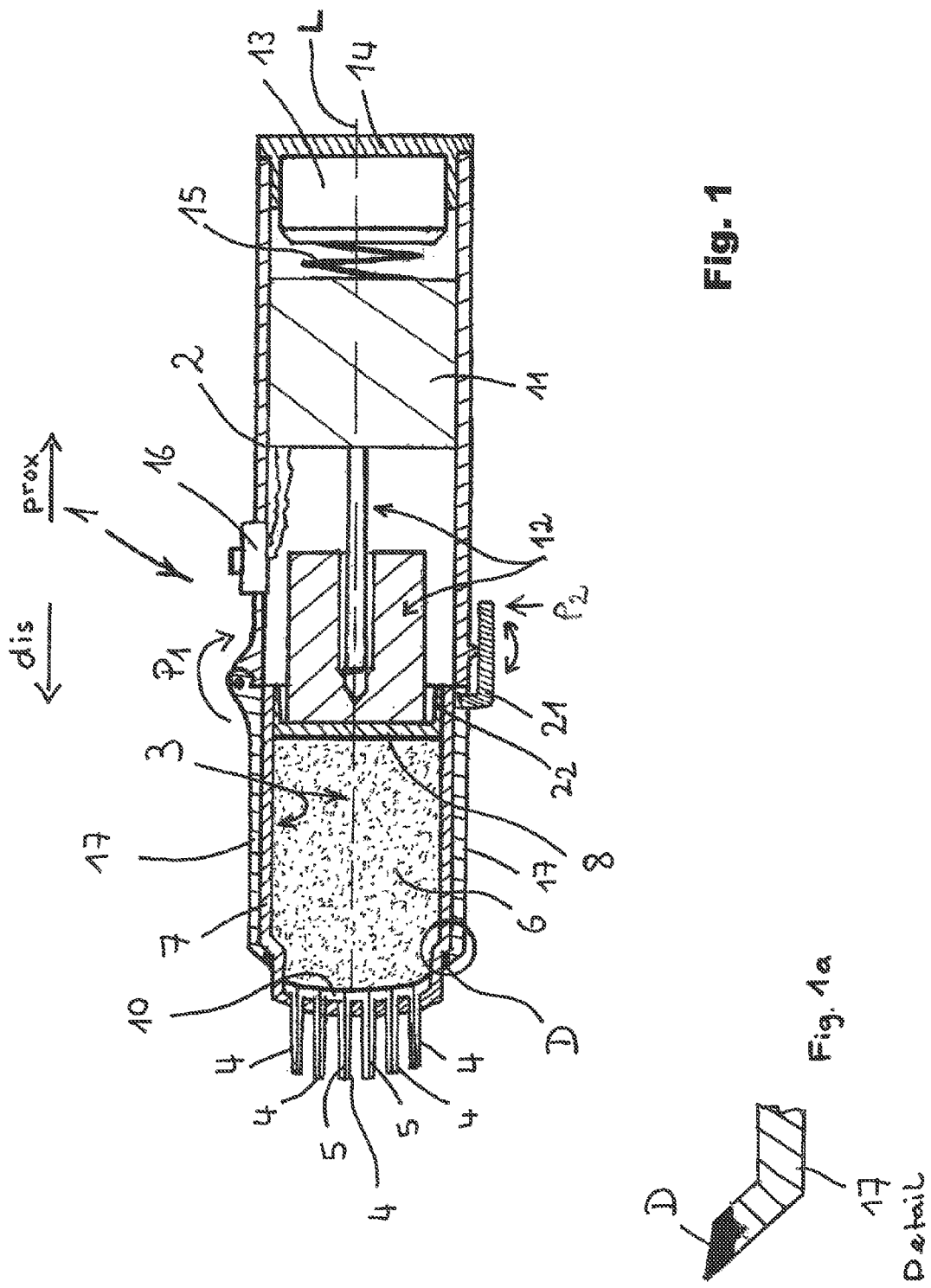
FIG. 1 shows an initial design example of the invented applicator as a cross-section along the longitudinal axis L.

Referring first to FIG. 1, applicator 1 comprises am applicator main housing 2 and a applicator housing top part 17. It is preferable that applicator main housing 2 accommodates a battery 13 using a normally separately removable battery compartment lid 14, and a motor 11. The battery 14 is normally electrically connected to the motor by a spring element 15, among other things.

The motor 11 is activated by the switch 16, whereby this is normally a micro-switch which is also accommodated in the main applicator housing 2, but which is not shown here in detail. Motor 11 drives a pressure element 12, which here comprises a body to be described as a thrust piece, with an internal thread into which a threaded rod driven by the motor engages. The said thrust piece is moved forward or backward depending on the motor's direction of rotation. If the thrust piece is moved forward, in the direction of the bristle-covered distal end of applicator 1, then it exerts pressure on the cartridge plunger 8 of the cartridge 3 which will soon be described in more detail.

The applicator housing top part 17 can be completely or partially removed from the applicator main housing without tools (meaning normally bare-handed) in order to gain access to the cartridge holding compartment. In this design example, the cartridge holding compartment is the internal area surrounded by the applicator housing top part. Generally speaking, it can be said that the cartridge holding compartment is predominantly, or better at least fundamentally, surrounded by the applicator housing top part. The front of the cartridge holding compartment has a cut-out area through which a section covered with bristles 4 of the actual cartridge (without a stem which acts as a pipe and which is located between the bristle facing and the cartridge itself) protrudes from the cartridge holding compartment, from the inside outwards. Preferably, the design of the cartridge and that of the cartridge holding compartment are customized to suit one another in such a way that, when the compartment is closed, the cartridge is held in the cartridge holding compartment without it rattling. For some applications, it is useful if the cartridge holding compartment is sealed from the outside against liquid penetration, this is dealt with in more detail later.

Figure 17:
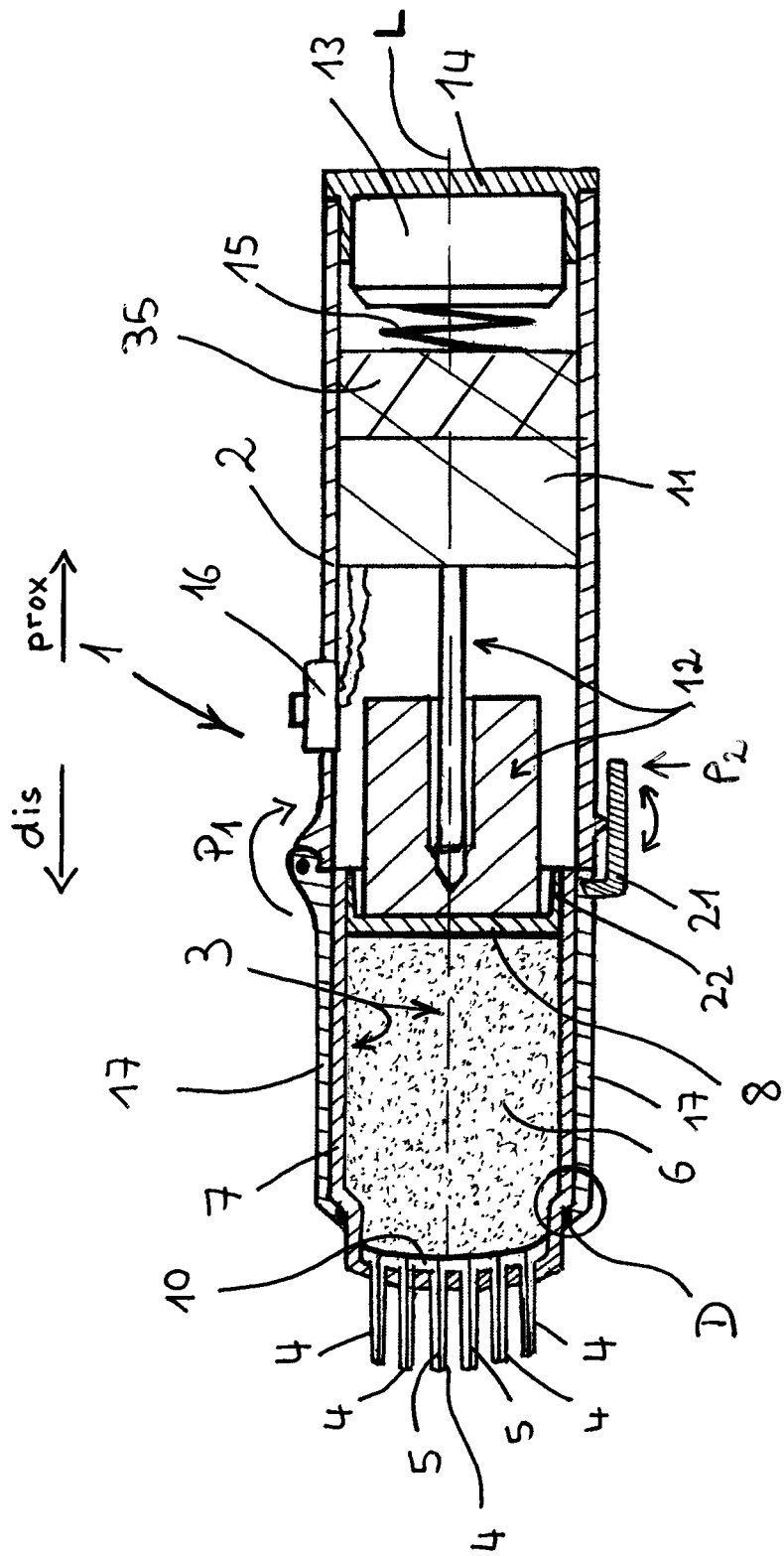
FIG. 17 shows the initial design example of the invented applicator as a cross-section along the longitudinal axis L with a vibrator.

In the design example shown in FIG. 1, the applicator housing top part 17 can be swung in the direction of the arrow P1 along an axis which is not described in more detail, and held against the applicator main housing 2. This swinging movement is normally hindered by the bar 21; once the bar 21 is pressed down in the direction of the arrow P2, it is however possible to swing the applicator housing top part 17 in the said manner. FIG. 17 shows the design example of FIG. 1 with a vibrator 35 included.

Alternatively, but not shown here, the applicator housing top part 17 can naturally also be held in place on the applicator main housing 2 with the aid of a snap lock or screw thread so that the applicator housing top part 17 can be released, for example, from the applicator main housing 2 with a screwing movement and can be ultimately removed by a movement in the direction parallel to the applicator longitudinal axis L. Similarly, it can be designed with a snap lock. Here it is conceivable, for example, that the applicator main housing 2 has a ring flange which encompasses applicator housing top part 17 and into which the latter can be locked—or vice-versa.

FIG. 1 shows that the said swinging capacity of the applicator housing top part 17 serves to allow a cartridge 3 to be inserted into the applicator 1.

It usually comprises a cartridge body 7 and a cartridge plunger 8 which is inserted in such a way that a seal is formed while simultaneously allowing it to be moved. The cartridge body 7 preferably has a circular cross-section. The maximum cartridge external diameter is preferably 8 mm to 20 mm. The maximum length of the cartridge (measured without bristle facing) in the direction parallel to the longitudinal axis L is preferably 5 mm to 35 mm, better only 5 mm to 20 mm. For single-dose uses, the invented cartridge and/or capsule are preferably designed to hold less than 10 ml, preferably less than 5 ml of the fluid to be applied. Its external size is adapted accordingly.

On its distal side facing towards the end with the bristles, the cartridge body 7 is preferably provided with a neck section with an external diameter which is smaller than the external diameter of the rest of cartridge body 7. When the cartridge is inserted and ready for use, the neck section and the bristles attached to it protrude outwards through the cut-out area in the cartridge holding compartment. With the aid of the ring shoulder formed between the neck section and the rest of the cartridge body 7, the cartridge supports itself against the applicator housing 2 and, in this design example, against the applicator housing top part 17, against the forces applied by the pressure element 12 acting in the direction parallel to the longitudinal axis L.

The cartridge 3 contains a specific amount of a fluid cartridge content 6, which is alluded to here by the dots. The cartridge content 6 is normally a thin fluid intended to be applied as a cosmetic and/or pharmaceutical. Preferably, but not exclusively, the term "low viscous" is used to describe a fluid with a viscosity of less than 100 mPa×s.

The cartridge 3 is characterized by its very simple construction which allows it to be manufactured very rationally from plastic in one or a few production steps.

The applicator 1 is preferably operated in combination with disposable cartridges 3. For many, in particular medical, applications, it is of particular benefit if the disposable cartridge is used as a so-called "single-dose" cartridge, i.e. the cartridge which is preferably sterile-packed until its use essentially only contains enough of the fluid to be applied as is needed for one single application Afterwards the cartridge is discarded together with the bristle facing attached to it. This way, even high hygiene requirements can be met inexpensively with the maximum ease of use through the motor-operated applicator which is not conceived as a disposable part.

The cartridge shown in FIG. 1 is characterized by that fact that the cartridge content 6 immediately comes into contact with the cartridge body 7 from the very beginning, i.e., the cartridge content 6 is filled directly into the cartridge 3 when the cartridge 3 is manufactured. Normally, the cartridge base 8 is only inserted afterwards to close the large, easy-to-use filling opening. For this purpose, the cartridge plunger 8 is designed so that it rests against the internal perimeter surface of the cartridge body 7 with the necessary pretension. To achieve this, the cartridge plunger 8 is preferably equipped with a ring collar 22 which can also be seen in FIG. 1. When unstressed, this ring collar 22 preferably runs, when viewed in relation to the longitudinal axis L, in a slightly slanted/tapered direction outwards. At the moment when the cartridge plunger 8 is pushed into the cartridge body 7 for the first time, the ring collar 22 which runs in a slanted, tapered direction outwards is simultaneously compressed and, as a result, rests against the internal perimeter surface of the cartridge body 7 with the correct pretension. Normally sufficient sealing power is achieved as a result without, for example, an additional sealing ring being required in the form of a separate cord seal.

In many cases, it is preferable if the cartridge plunger 8 fits the shape of the neck section of the cartridge body 7, i.e. has an internally projecting section with a reduced external diameter which can run into the section with the reduced diameter formed by the neck and thus provide an improved and complete emptying of the cartridge. Also compare to FIG. 10.

The cartridge body 7 is connected to the bristles 4 to form one single piece, i.e. the bristles 4 cannot be non-destructively separated from the cartridge body 7. The cartridge body and the brushes form a refill unit which are to be handled together.

The service life of the applicator as a whole is not limited by the service life of the bristles, or through the period of use permitted under bacterial contamination considerations.

In the design example for cartridge 3 shown for FIG. 1, each of the bristles 4 is hollow inside and thus creates a bristle channel 5 which stretches through the bristle 4. This is a design which is advantageous for a number of applications as it achieves an optimum distribution of the material to be applied which, in some cases, is extremely expensive and thus needs to be used with a maximum of economy. In other cases, in which the focus is less on the economical use of the fluid to be applied and more on achieving the most inexpensive cartridge manufacture possible, the latter should preferably only have a single hollow bristle.

The bristle channel 5 not only passes through the bristles 4, but also through the bristle base layer 10 located on the inside of the distal end wall of the cartridge body 7. This bristle base layer 10 is made up of the same material as the bristles, is connected to the bristles 4 to form a single piece and penetrates the distal end of the cartridge body 7, which usually originates in the manufacturing method just about to be described in more detail. Each of the bristle channels 5 is alluded to here only through a thin, black, unbroken line which extends in the middle through the bristles 5 and the bristle base layer 10.

It is particularly preferable if the diameter of the bristle channels 5 is adjusted in relation to the cartridge content 6 so that the capillary action of the bristle channels prevents the cartridge content 6 from escaping through the bristle channels as long as the cartridge content 6 is not put under pressure. However, such a design is not imperative. Alternatively, that is to say, in particular if the bristle channels 5 have a larger diameter, they can also be closed using a cap 25 which has been designed accordingly, compare to FIGS. 4 to 6, 9, 10 and 14.

To dispense the cartridge content 6 in the course of the application, the user presses the switch 16. This activates the motor which then advances the body already described above in the direction of the cartridge plunger 8 and then, together with the cartridge plunger 8, ultimately moves in the direction of the distal end of the applicator 1. This reduces the volume available to the cartridge content 6. In the cartridge content 6, pressure builds up which then dispenses a part of the cartridge content 6 through the bristle channels 5 and into the open. Thus, the cartridge content 6 exits at the tip of the bristles 4.

It is clear that, thanks to this, the cartridge content 6 can be applied with particular success and largely without loss to the hair-covered skin areas, whereas with conventional means—for example in conventional applications using a cotton bud—a lot of the substance would be lost and the hairs would get unnecessarily stuck together.

A bristle in the sense of the invention refers to—in technical terms—a bending rod which is stressed on one side and whose maximum diameter, Dmax, is above the rounding radius, i.e. the bristle root, with which the bristle emerges into the foundation ground which supports it, is at least 5 times, or better at least 10 times smaller than the maximum length, Lmax, of the bristles in the direction parallel to its middle longitudinal axis, BL. Ideally, the bristle is flexible enough to allow its tip—based on the gradient of its middle longitudinal axis, BL, when unstressed—to be reversibly deflected by the forces which occur during the intended application by at least the distance AL, perpendicular to the middle longitudinal axis, BL. Ideally, each bristle is equipped with a jacket surface which is tapered or slanted in relation to the bristle longitudinal axis, BL, and which is preferably at an angle $\alpha$ of between 0.5° and 2.5° to the bristle longitudinal axis. This applies not only for the design example explained here, but for all design examples.

The bristle facing is normally not tufted, i.e. the bristles are not implanted in groups in the foundation ground which supports them, but rather each individual bristle has an all-round clearance between it and the adjacent bristles in the area of the bristle base. The bristles are also not normally arranged in a straight line, one after another, like a comb, but are preferably arranged in sequence in several rows which each form a self-contained circular ring line. At the same time, the several circular ring lines are mostly arranged concentrically within one another. Ideally, not only individual bristles are envisaged, but rather a bristle array comprising between 12 and 30 bristles. Each of these preferably has one middle longitudinal axis which runs parallel to the applicator longitudinal axis, L. The bristles are preferably manufactured from a soft-elastic material.

To manufacture the bristle facing shown here, which is characterized by the fact that its bristle base layer 10 is heat sealed with the internal surface of the distal front end of the cartridge body 7, there are different options.

The first option is to injection mold the cartridge body 7 in the first injection mold step, whereupon the cartridge body 7 initially remains open at the side into which the cartridge plunger 8 is inserted later. Holes generated using corresponding pins included on one of the mold halves, are already made in the distal front end of the cartridge body 7 in this step. Next, the mold half bearing the said pins is removed. Instead, another mold half is mounted which has narrower pins and which penetrate into approximately the center of the holes already left in the cartridge body 7 by the afore-mentioned pins and provide a seal against the core still arranged in the cartridge body 7. Then, a second plastic mass which forms the bristles 4 is injected normally from the inside of the cartridge body 7. The second plastic mass then forms the bristle base layer 7 at the internal surface of the distal front end of the cartridge body 7 and flows through the ring gap which remains free between the holes in the front end of the cartridge body 7 and the pins of the second mold half that protrude through them, and into the bristle-forming cavities in the second mold half.

Once the second plastic mass has set, the second mold half with its narrow pins is removed. The narrow pins leave a bristle channel 5 in each of the bristles 4. Finally, the cartridge body 7 is completely removed from the mold by pushing it off the core still located inside of it.

An alternative option for forming the brushes 4 with an approximately central bristle channel 5 shown in FIG. 1 is as follows:

First of all, the cartridge body 7 (without cartridge plunger 8 which is inserted later) is injected in such a way that the cartridge body 7 initially has a completely closed front end. Then, the exterior of the mold half limiting the front end of the cartridge body 7 is removed and replaced by another mold half which has well ventilated cavities for forming bristles. The second plastic mass is now injected again from the side of the mold core located in the cartridge body 7. This backs up at least for a brief moment in front of the closed end wall of cartridge body 7 so that a high pressure is formed. Under the influence of this high pressure and possibly also of the high temperature of the just-injected second plastic mass, the second plastic mass locally punctures the front end of the cartridge body 7—namely everywhere where the front end of the cartridge body 7 is lying "hollow", i.e. over a cavity arranged on the exterior and used for forming the bristles. Once punctured, the second plastic mass shoots through the openings formed by itself in the cartridge body 7 and into the bristle forming channels. When the mold halves holding the bristle forming channels are cooled, the second plastic mass firstly sets in the edge area of the mold and each bristle still has a core of liquid plastic mass. If compressed air is injected here at the right moment, it will force it through the still molten core and thus, when flowing in the direction away from the inside of the cartridge, create a bristle channel 5 in each bristle 4. Such a method is particularly rational as the amount of molding is kept low. The only thing required is skill to determine at what moment air needs to be blown in to successfully drive out the still molten bristle core. This skill can only be acquired by a professional by performing trials, for controlling the correct moment depends on different boundary conditions in each individual case and thus generally accepted information cannot be supplied.

A claim regarding independent protection is also being made for this procedure.

It must be emphasized that not least the specifications explained above for the bristle facing and its manufacture are advantageous for all design examples.

FIG. 2 shows an alternative design option for cartridge 3. This cartridge also comprises a cartridge body 7 and a cartridge plunger 8, which is preferably designed as described above for the first design example. In particular, the cartridge plunger 8 rests against the inside surface of the cartridge body 7 so that it forms a seal, as described above.

In contrast to the first design example, the cartridge content 6, however, is not filled immediately into the cartridge 3 during manufacture, with the result it would immediately come into contact with the inside surface of the cartridge body 7 and/or the cartridge plunger 8. Instead, the cartridge content 6 is filled into an hermetically sealed capsule 18, preferably a capsule made out of film or a gel shell, subsequently generally referred to as a "capsule".

In contrast to cartridge 3 of the first design example, this cartridge 3 is preferably provided in the area of its distal front edge, with at least one—and preferably only one—mandrel 9 on the inside, which ideally forms a passage outwards. Once the plunger 8 is pushed towards the distal end of the cartridge 3 for the first time, the capsule 18 is pressed against the mandrel 9 which ultimately punctures it. This way, the cartridge content 6 can then be dispensed into the open via the passage created here by the mandrel 9. Filling the cartridge 3 with the aid of such a capsule 18 has the major advantage that it can be ensured that the cartridge content 6 is protected from any contact with its surroundings until the cartridge 3 is definitively punctured. This is of great importance in particular for pharmaceutical applications, but also for cosmetic applications. This way, not only the hygienic integrity can be guaranteed, but also usually also a considerably slower deterioration of the cartridge content 6, which can be protected as far as possible against air admission—of course with the exception of diffusion processes which cannot be completely prevented.

The facing of the bristles 4, which, in this design example is combined with cartridge body 7 to form one single piece, meaning that they are inseparable, is characterized here as being another optional manufacturing method.

A bristle base layer 10 is also envisaged here, however it is not heat sealed with the external surface of the distal front end of the cartridge body 7. The individual bristles 4 emerge from this bristle base layer 10.

Preferably, only one of the bristles 4 is provided with a bristle channel 5 here, namely ideally the central bristle which interacts with the mandrel 9. This bristle is preferably at least 30% thicker than the other bristles.

This bristle facing was manufactured as follows:

First of all, a cartridge body 7 was injection molded here with a completely closed distal front end. The only exception is the interior of the mandrel 9 which was kept free right from the beginning with the aid of a suitable molding pin on the tool. Once the cartridge body 7 was injection molded, the molded part which formed the distal front end of the cartridge body 7 was removed. Instead, now one mold half was fitted here, the one with the cavities used for forming the bristles and which, in the area of the central bristle, incorporates the mandrel type pusher which protrudes through the front end of the bristle body 7 in the area of the mandrel 9 and which preferably belongs to the mold core which is positioned in the inside of the cartridge body. Thereafter, in a second step, a second plastic mass was injected which fills the cavities forming the bristles and forms the bristle base layer 10. The hot, second plastic mass adheres to or is heat sealed with the surface of the already cooled plastic mass which forms the cartridge body 7 so that it results in the said one-piece design. It is then removed from the mold.

In the same way as in the first design example, a soft elastomer is also preferably used for the bristles 4 in this design example. In this second design example, it must still be noted that limiting the inclusion of a bristle channel 5 to only the central bristle and thus only dispensing the cartridge content to the central bristle has its advantages. For this method prevents the dispensed cartridge content 6 from escaping laterally from the area of the bristle array which would mean that is it no longer available for massaging into the skin.

For this reason, a design example which is not shown here with a figure, but which is a preferred, involves the combining of the first and second design examples to the effect that no capsule is provided in the cartridge 3, but instead the cartridge content is filled directly into the cartridge 3 whereupon the dispensing is then performed, differently to in the first design example, only via one central bristle, as in the second design example. If a capsule 18 is omitted, this immediately has the advantage that the cartridge content can be sealed better—a cap set onto the bristles, as will be explained later, which only needs to seal off one of the bristles, is easier to create than a cap which seals off all of the bristles.

FIG. 3 shows a third design example for an invented cartridge. The cartridge here almost completely corresponds to the second design example which is why the statements made there regarding the cartridge and the manufacturing method of the bristles also correspondingly apply for this cartridge, unless the differences expressly specified in the following result in something else.

The difference between the second design example and the third design example lies in the fact that the mandrel 9 is not connected to a bristle, but rather ends on the outside, as shown in FIG. 3, within the bristle array which has a groove in the area of the mandrel 9. This way, the cartridge content 6 can be dispensed into an area which is defined by closely standing bristles and is practically self-contained. The mandrel 9 preferably forms an extension which protrudes outwards. The extension creates a slightly malleable pipe flange which can be easily sealed with the aid of a subsequently fitted cap.

If FIGS. 2 and 3 are compared directly, it is possible to still see how the clear internal diameter of the mandrel 9 can be varied in order to adjust the viscosity of the cartridge content 6 this way. For the clear cross-section of mandrel 9 must not be too large. This is the only way of preventing the cartridge content 6 from unintentionally leaking once the capsule 18 has been pierced. It is also applicable here that the clear cross-section preferably needs to be sized so that the capillary action of the mandrel 9 prevents the cartridge content 6 from leaking into the open as long as pressure is not applied to the cartridge content 6 by the cartridge plunger 8.

Figure 4:
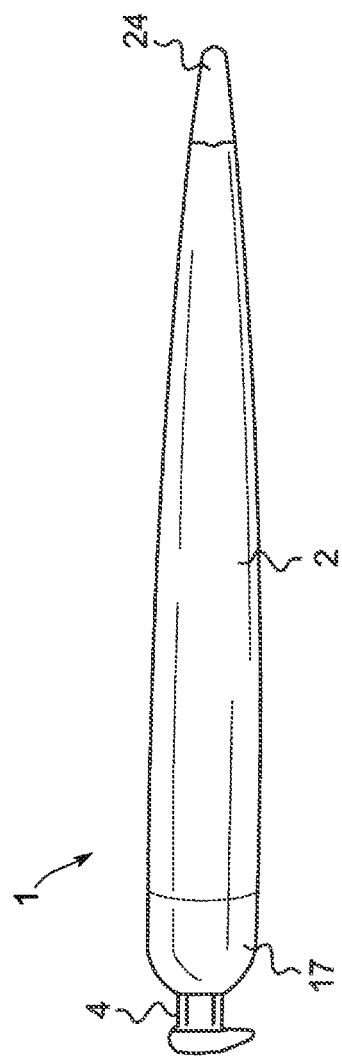
FIG. 4 shows a second design example of the invented applicator, viewed from above.
Figure 5:
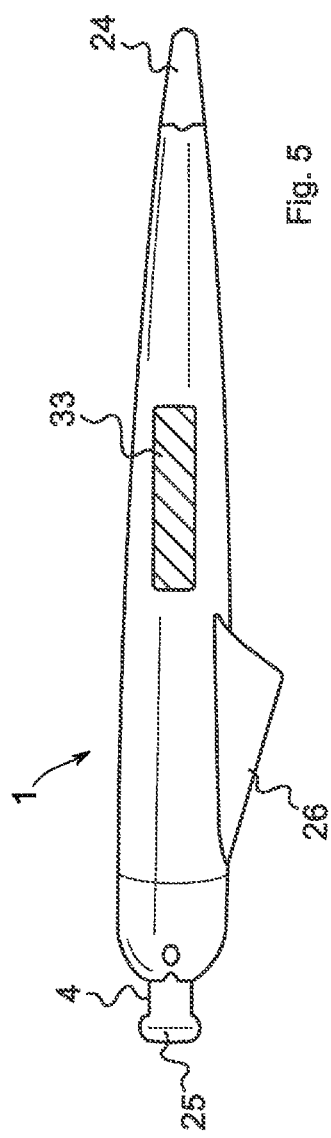
FIG. 5 shows a second design example of the invented applicator, viewed from the side.
Figure 6:
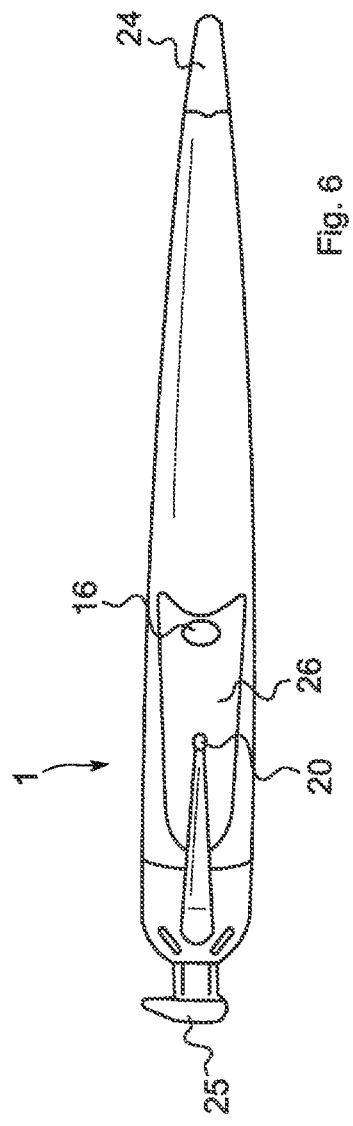
FIG. 6 shows a second design example of the invented applicator, viewed from below.
Figure 8:
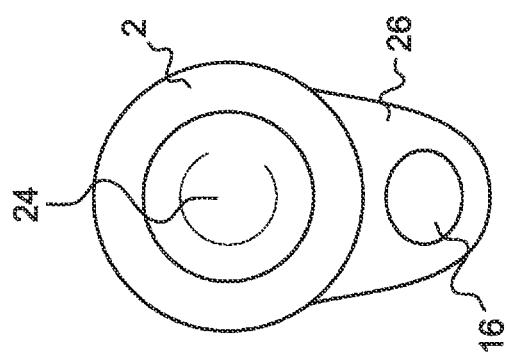
FIG. 8 shows a second design example of the invented applicator, viewed head-on from the rear.
Figure 7:
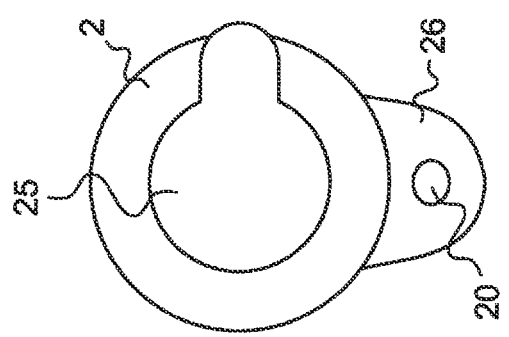
FIG. 7 shows a second design example of the invented applicator, viewed head-on from the front.

FIGS. 4 to 6 show a special design example for a both elegant and functionally-structured design example for an applicator housing 2 with an application housing top part 17. In principle, this design example also corresponds to the design example already described. For this reason, the information given above also applies for this design example unless the differences expressly specified in the following result in something else.

One difference to the first design example is that the applicator main housing is designed here in such way that it becomes narrower and narrower the closer it gets to the proximal end which is the end facing away from the bristle facing. It preferably ends in an elastomer tip 24 which ideally accounts for less than 50 percent of the maximum diameter of applicator 1. This elastomer tip 24 can be used to massage in the cartridge content 6 applied beforehand with the aid of the bristles 4.

The applicator top part 17 can be easily recognized here. It is developed here preferably as a screw-on top part. Otherwise, the cartridge 3 is however fitted in the way already described for the first design example. As can be seen, the applicator main housing 2 can be used very well as an advertising medium and information carrier if printed or if a corresponding label 33 is adhered to it.

As can be easily recognized here, the bristles 4 are protected and sealed by a cap 25 until opened.

The switch 16 is designed differently here than in the first design example. Here, the switch 16 is preferably arranged in a radial direction in relation to the longitudinal axis L, clearly outwards over the protrusion 26 which projects over the surrounding surface of the applicator main part. This not only creates additional space for the switch 16 and the electronic board which may be assigned to it, but simultaneously acts as a thumb stop during use. This ensures that the applicator is held in an ergonomically correct fashion and, at the same time, the switch 16 can be easily operated.

The aforementioned protrusion 26 preferably simultaneously houses a lamp 20, ideally in the shape of a LED, which allows the area on which the substance is to be applied to be lit up. This is particularly perceived as being convenient if the applicator 1 is used to allow a practitioner or other person to administer an application.

The external surface of the applicator housing 2, of the applicator housing top part 17 and that of a battery compartment lid 14, if provided, are ideally metal coated. This guarantees that the applicator can be cleaned particularly well and, if necessary, can be treated with a disinfectant, whereupon any residual contamination would be seen immediately on the metal coating.

FIGS. 9 and 10 once again show the cartridge 3 used in the first design example as a single view.

Figure 11:
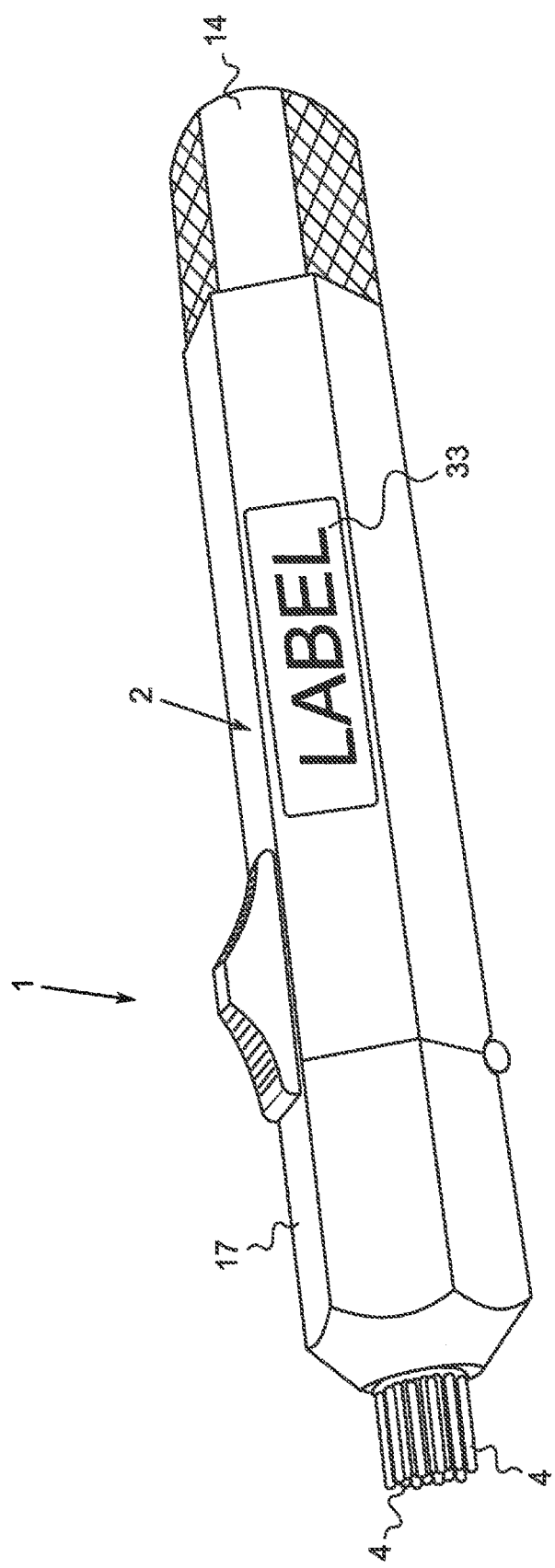
FIG. 11 shows a third design example of an invented applicator, viewed at a slant from the side, in an operational condition.
Figure 12:
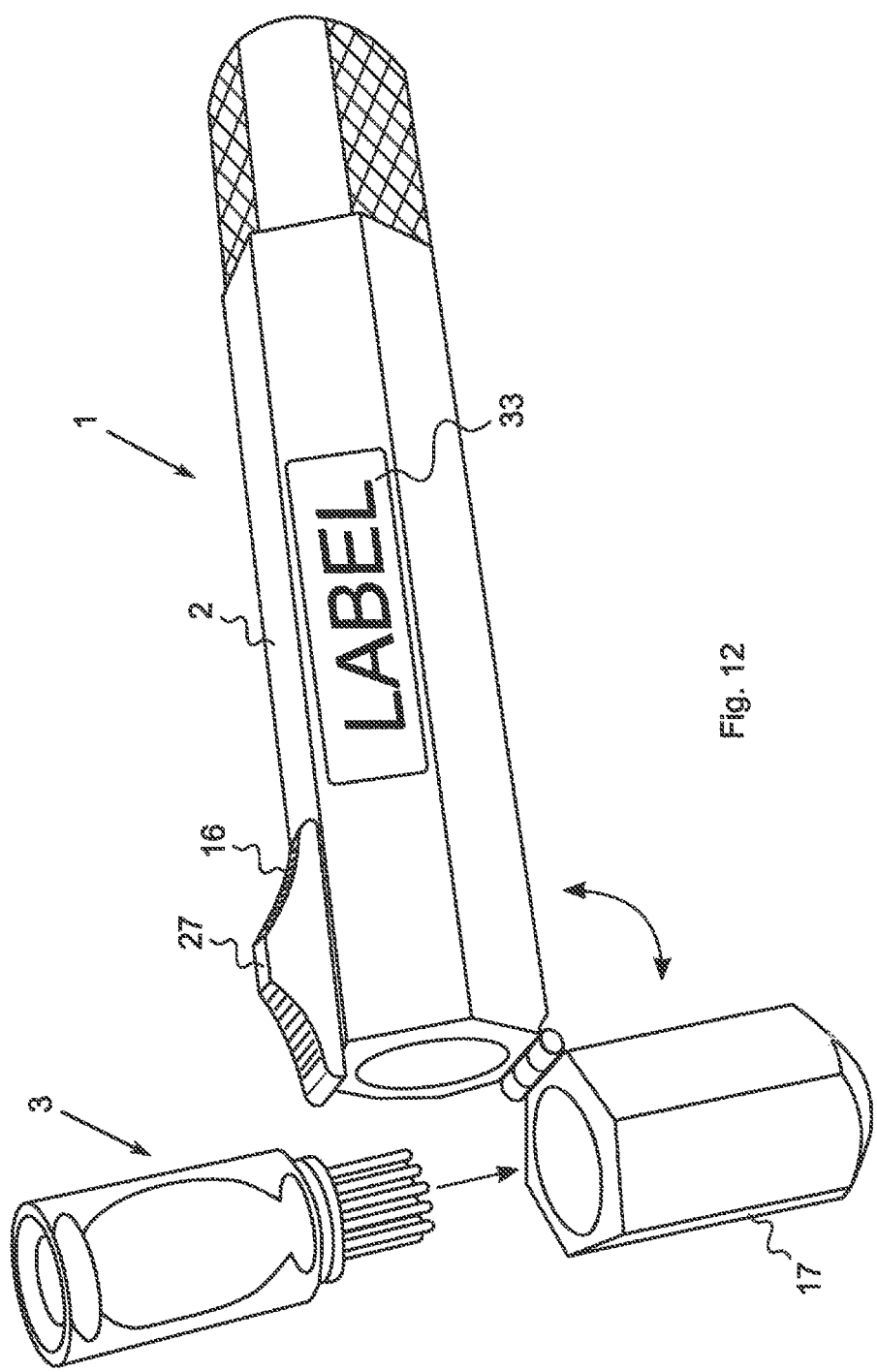
FIG. 12 shows the applicator according to FIG. 11, with the lid opened for refilling the cartridge.

FIGS. 11 and 12 shown another design example which is almost completely identical to the first design example, meaning that the information provided for it also applies for this design example unless the differences expressly specified in the following result in something else.

FIGS. 11 and 12 once again provide quite a good view of how the applicator 1 is divided up into an applicator main housing 2, an applicator housing top part 17, and preferably also a battery compartment lid 14. As can be seen here once again, the applicator main housing 2 can be used very well as an advertising medium and/or information carrier if printed or if a corresponding label 33 is adhered to it.

As is already the case in the first design example, the applicator housing top part 17 is linked to the applicator main housing 2 in a way which allows it to be swung back and forth on one side, so that the applicator housing top part 17 can be flipped open in a similar way to the barrel of a shotgun in order to insert a (new) cartridge 3.

As can be seen in FIG. 12, a cartridge as described within the framework of the second design example is used here. A cartridge as described within the framework of the second design example can alternatively be used here.

As can be easily recognized in FIG. 12, a special arrangement is used for the switch 16. The switch 16 is housed in a sliding element 27 which is simultaneously used for locking the applicator housing top part 17 which can be swung open.

For all of the design examples described here, it can be advantageous if the entire applicator housing, or at least the applicator housing in the area where it is penetrated by the cartridge and its bristle facing, has a sealed-off design so that the distal end of the applicator 1 with the bristle facing of the cartridge can, for example, be held and washed out under a jet of water without the water penetrating into the applicator 1. To achieve this, it may be preferable, for example, at the cartridge and/or at the applicator housing top part 17. in the area where the cartridge 3 penetrates the applicator housing 17, to provide a seal D which prevents water entering through the gap between the applicator housing top part 17 and the corresponding area of the cartridge 3. Such a seal D can, for example, look like the seal shown in FIG. 1*a* which is an enlargement of the area marked in FIG. 1 with a circle. Around the cut-out area of the applicator housing top part, through which the neck section of the cartridge with the attached bristle array protrude, a lip-like seal D made of a flexible material is sprayed on.

Of course, it is particularly preferable if a seal is applied to the joint between the applicator housing top part 17 and the applicator main housing 2, one which prevents for example the penetration of the water used for rinsing here.

Figure 16:
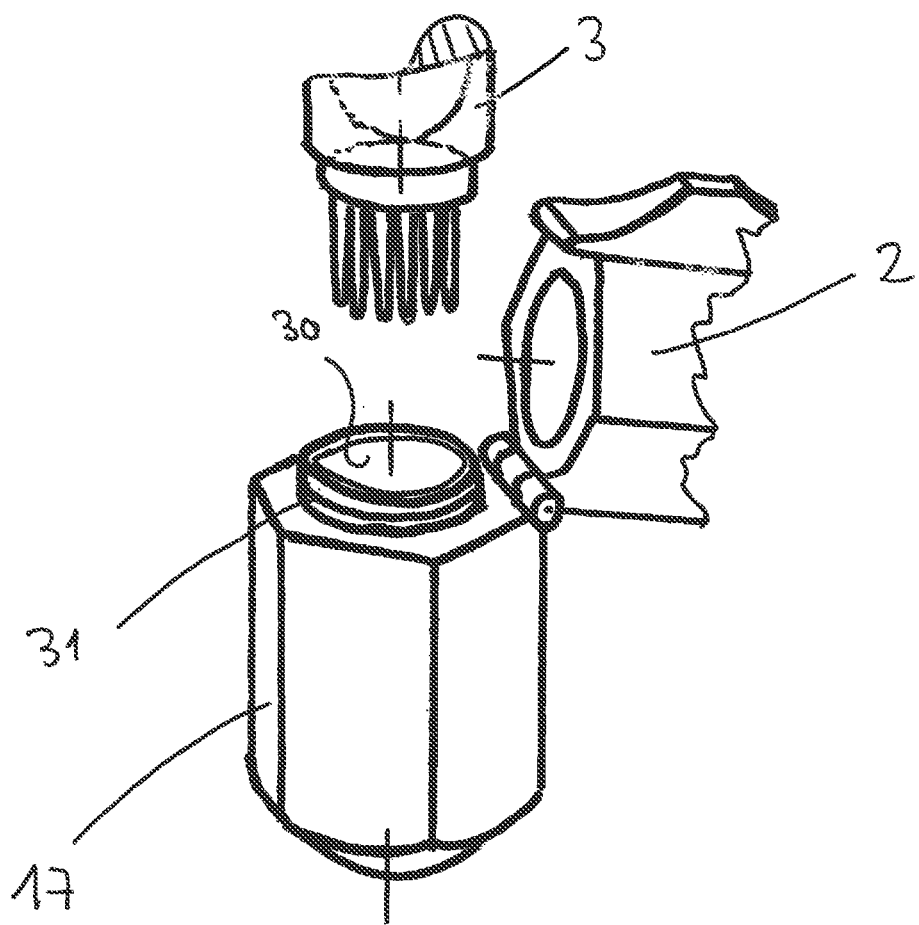
FIG. 16 provides a proposal for the improved sealing of the applicator body top part in relation to the applicator main body for the design example illustrated in FIG. 12.

Such a seal can be achieved with particular ease through the fact that, for example, the applicator housing top part 17 has a ring collar 30 for insertion into the applicator main housing 2 which bears a cord or lip seal 31 and which rests against its interior surface at the moment when the said ring collar 30 is incorporated in the applicator main housing, compare to FIG. 16.

For some applications, it is particularly preferable if the applicator or the applicator main housing 2 not only include the battery, motor and pressure element 12, but for example also contain a vibration element which creates oscillations, and preferably the kind of oscillations which essentially move in the direction perpendicular to the longitudinal axis L. The applicator 1 can then be immediately used in order to, with the aid of fast, short-stroke movements, massage in the cartridge content 6 dispensed into the open and preferably take this opportunity to stimulate the skin area to be treated.

Figure 13:
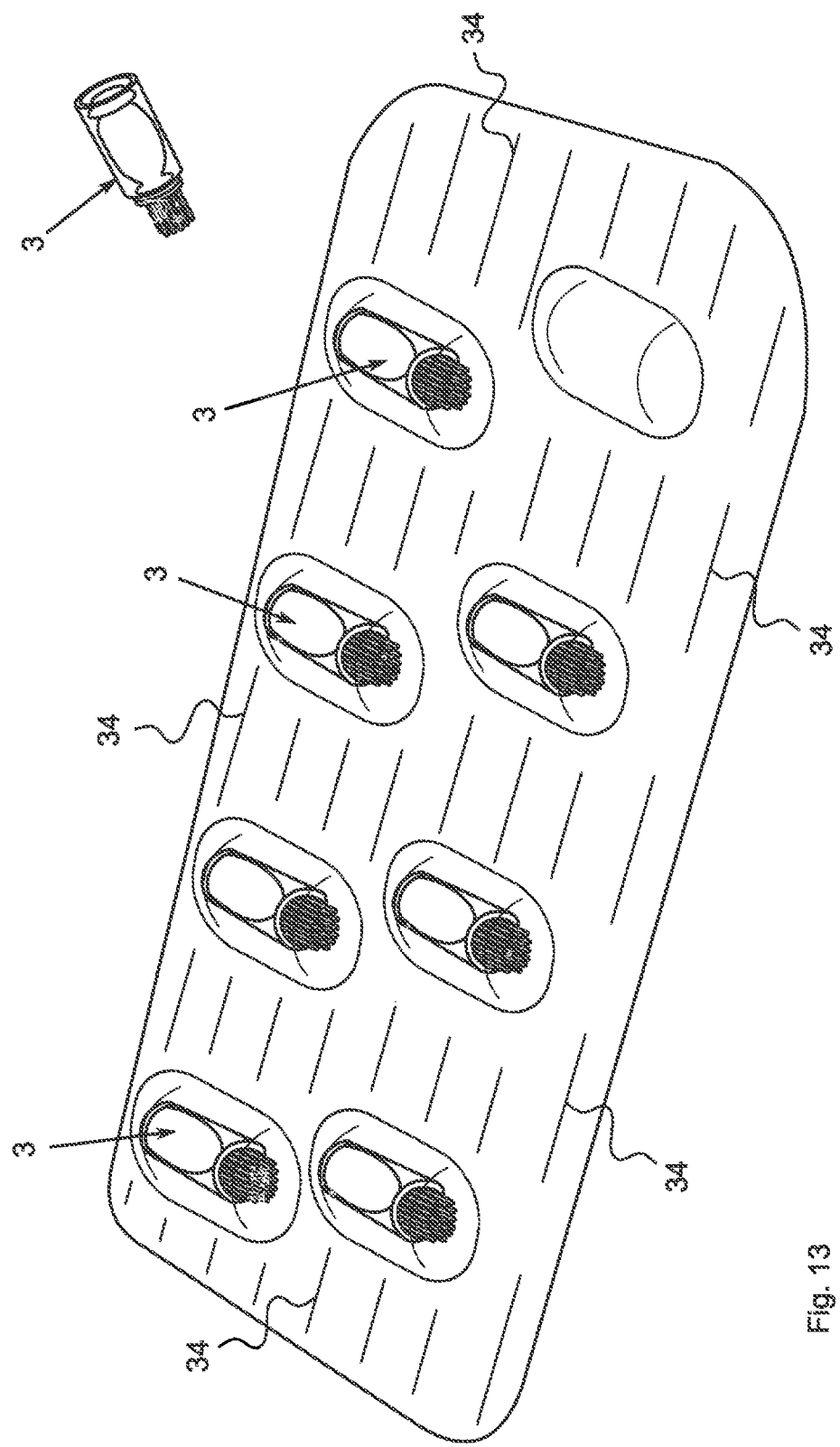
FIG. 13 shows a blister pack which provides an air-tight supply of a number of cartridges, whereupon one of the cartridges has been pushed through the blister and removed.

Particularly in those applications where the cartridge content 6 requires a special degree of protection, it makes sense to combine the invented applicator 1 and the cartridge required to for use in combination with it to form a system in which the cartridge 3 is integrated and stored in so-called blister packs. These blister packs are widely recognized through their use in pill packaging. They normally comprise a plastic carrier with individual recesses, each of which preferably holds a cartridge 3. Once this plastic carrier has been filled with the cartridges, the reverse side of the plastic carrier is preferably sealed with a thin metal foil which is fused with the plastic. To remove a cartridge to refill the applicator 1, the cartridge is pushed out through the metal foil. The other cartridges 3 still remain in their recesses in the plastic carrier, protected by the metal foil. This is shown in FIG. 13. It must also be noted that the plastic carrier is also well suited for use as an advertising medium and/or information carrier by applying lettering 34 onto its free spaces, as implied in FIG. 13 by a number of black lines.

Figure 14:
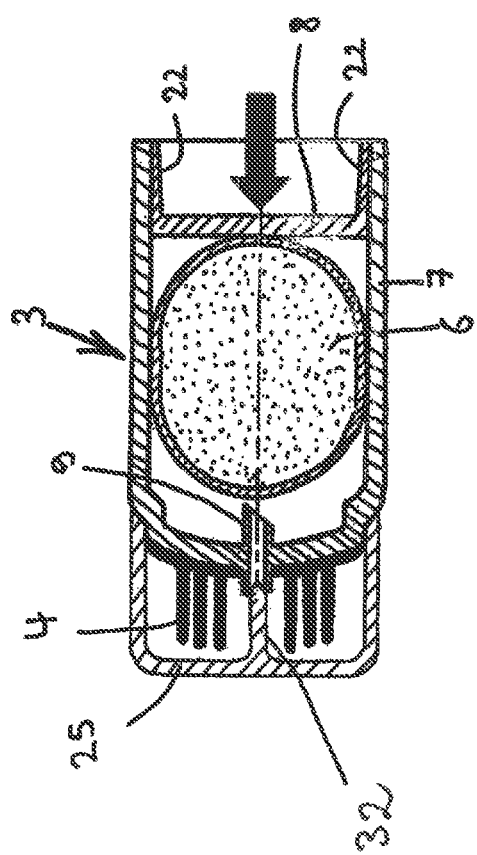
FIG. 14 shows an example of a cap.
Figure 15:
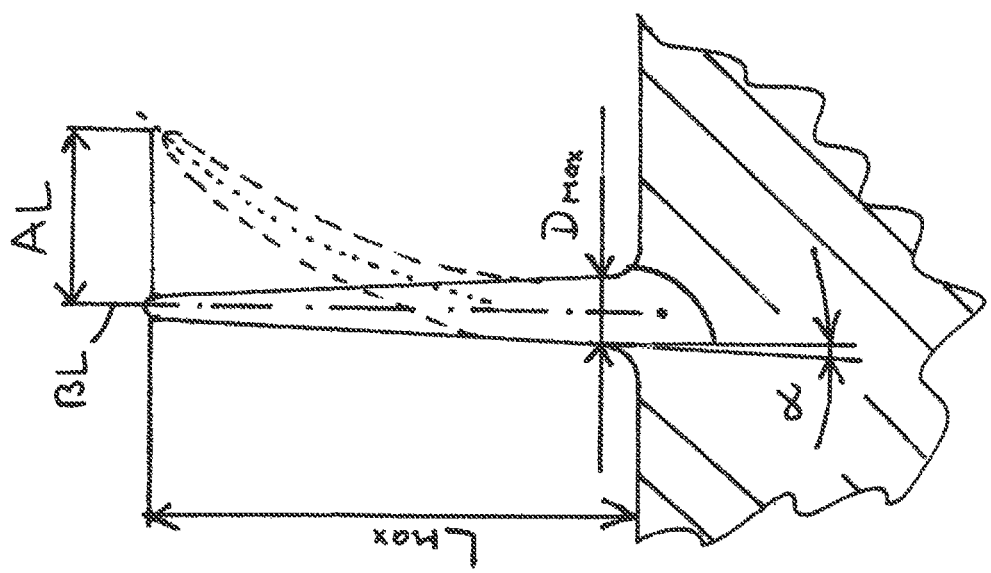
FIG. 15 explains, in a way which is valid for all the design examples, what a bristle preferably means in the sense of the invention.

It must also be noted that the invented system, as already mentioned, is also good for use in the application of skincare products, salves and creams onto hair-free skin. If these products have a higher viscosity (as is mostly the case), they can be accommodated through the corresponding enlargement of the clear cross-section on the internally hollow bristle (4). For this purpose, the solutions wherein only one central bristle is hollow on the inside are especially preferred. FIG. 14 shows an example of a cap 25 which can be used for sealing purposes. The cap can be attached to the cartridge, in particular by being clipped on or snapped on. The cap has a sealing element 32, which is designed here as a mandrel, which can be spread into the neck of the dispensing opening or pressed against it and via which the fluid to be applied can be dispensed into the bristle facing. This way, the neck is protected and preferably also sealed. This is particularly practical when the cartridge is not only a mono-dose unit and/or the fluid to be applied is immediately filled into the cartridge, without the use of a capsule.

A similar cap can also be used if, or example, a cartridge bearing a bristle facing is used, as shown in FIG. 2. At least at its outermost area, the mandrel preferably takes on the shape of the tube put over the bristle through which the fluid to be applied is dispensed—preferably in such a way that the said sleeve area surrounds the hollow bristle to form a seal.

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

LIST OF REFERENCE NUMBERS

1 Applicator
2 Applicator main housing
3 Cartridge
4 Bristle
5 Bristle channel
6 Cartridge content
7 Cartridge body
8 Cartridge plunger
9 Mandrel
10 Bristle base layer
11 Motor
12 Pressure element
13 Battery
14 Battery compartment lid
15 Spring element
16 Switch
17 Housing top part
18 Capsule
19 Not allocated
20 Lamp
21 Bar
22 Ring collar
23 Not allocated
24 Elastomer tip
25 Cap
26 Protrusion
27 Notch
28 Not allocated
29 Not allocated
30 Ring collar
31 Seal, preferably in the form of a cord or lip seal
32 Sealing element
33 Label (advertising sticker, print, or similar)
34 Lettering
L Applicator longitudinal axis
D Preferably sprayed-on, soft-elastic seal
dis distal
prox proximal
P1 Swing arrow
P2 Pressure arrow
BL Bristle longitudinal axis
Lmax Maximum bristle length
AL Bristle deflection
D Seal
Dmax Maximum bristle diameter
α Angle

I claim:

1. A cosmetic or pharmaceutical applicator brush comprising
a supply of a cosmetic or pharmaceutical fluid provided in the brush, the outside of the brush having a bristle facing, a pump mechanism for dispensing the fluid through or in the bristle facing, characterized by the fact that the bristle facing of the brush is a fixed component of a cartridge which keeps a supply of the fluid ready for use and which can be inserted into and removed from an intended compartment of the brush preferably without the use of tools; and
wherein, when in an unused state, the cartridge holds a capsule made up on a tightly sealed shell, preferably in the form of a film or gel shell, which is filled with the fluid to be applied.

2. The brush of claim 1, wherein the cartridge is a disposable cartridge.

3. The brush of claim 1, wherein the cartridge has at least one mandrel protruding into its interior which pricks open the shell of the capsule once the pump mechanism is started up to dispense the fluid.

4. The brush of claim 3, wherein the mandrel has a non-rotund cross-section.

5. The brush of claim 3, wherein the mandrel has a cross-shaped cross-section.

6. The brush of claim 1 wherein the cartridge is essentially made up of a harder first plastic which at least forms the perimeter walls and one end wall of the cartridge, and a softer, preferably flexible or rubbery-elastic second plastic which forms the bristles inseparably connected to the cartridge.

7. The brush of claim 1 wherein the bristle facing comprises at least one bristle which is hollow and has a bristle channel, the bristle channel connecting the interior cartridge compartment holding the fluid to be applied to the surroundings of the brush.

8. The brush of claim 1 wherein a side of the cartridge facing away from the bristle facing has a base and cartridge plunger which can slide back and forth like a piston, whereupon this is preferably manufactured from a third plastic whose elasticity lies between the plastic forming the bristles and the plastic forming the perimeter wall of the cartridge.

9. The brush of claim 1 wherein a vibrator, which causes the brush and the bristle facing to vibrate, is fitted in the brush body preferably in the direction of its longitudinal axis.

10. A system for the application of cosmetics, comprising a brush according to claim 1 and a number of cartridges which are not refillable without the use of tools, each cartridge containing a supply of cosmetic and designed to suit the cartridge-holding compartment of the brush.

11. The system of claim 10, wherein several of the cartridges are grouped together in a blister pack to provide a cartridge supply, whereupon the blister pack is structured so that each of the cartridges can be individually removed from the blister pack without subjecting the other cartridges to largely unhindered air admission.

12. A cosmetic or pharmaceutical applicator brush comprising
a supply of a cosmetic or pharmaceutical fluid provided in a brush, the outside of the brush having a bristle facing, a pump mechanism for dispensing the fluid through or in the bristle facing, characterized by the fact that the bristle facing of the brush is a fixed component of a cartridge which keeps a supply of the fluid ready for use and which can be inserted into and removed from an intended compartment of the brush preferably without the use of tools; and
wherein a bristle channel is formed in a hollow bristle of at least one bristle of the bristle facing, the bristle facing designed to be narrow enough so that the fluid contained in the cartridge is prevented by capillary action of the bristle channel from leaking through the bristle channel into the open as long as excess pressure is not applied to the cartridge.

13. A cosmetic or pharmaceutical applicator brush comprising
a supply of a cosmetic or pharmaceutical fluid provided in a brush, the outside of the brush having a bristle facing, a pump mechanism for dispensing the fluid through or in the bristle facing, characterized by the fact that the bristle facing of the brush is a fixed component of a cartridge which keeps a supply of the fluid ready for use and which can be inserted into and removed from an intended compartment of the brush preferably without the use of tools; and
wherein the inside of an end wall of the cartridge is at least partially covered by a layer of the plastic which forms bristles, whereupon this layer is connected to the bristles through local perforations in the plastic forming the cartridge to create one material and one single part.

14. A cosmetic or pharmaceutical applicator brush comprising
a supply of a cosmetic or pharmaceutical fluid provided in a brush, the outside of the brush having a bristle facing, a pump mechanism for dispensing the fluid through or in the bristle facing, characterized by the fact that the bristle facing of the brush is a fixed component of a cartridge which keeps a supply of the fluid ready for use and which can be inserted into and removed from a brush chamber of the brush preferably without the use of tools; and
wherein the brush chamber incorporating the cartridge is accessible by flipping open a part of the brush body away from another part of the brush body along a hinge axis which is fundamentally perpendicular to a longitudinal axis of the brush.

* * * * *